US011912691B2

(12) United States Patent
Kern et al.

(10) Patent No.: US 11,912,691 B2
(45) Date of Patent: Feb. 27, 2024

(54) TOCOTRIENOLS DERIVATES, METHODS AND USES THEREOF

(71) Applicant: GLOBAL SCIENTIFIC, Reno, NV (US)

(72) Inventors: Daniel Kern, Reno, NV (US); Kent Mirkhani, Reno, NV (US); Ivo Manuel Ascensão Aroso, Perafita (PT); Ricardo De Sá Bessa, Matosinhos (PT); Rui Luis Goncalves Dos Reis, Oporto (PT)

(73) Assignee: GLOBAL SCIENTIFIC, Reno, NV (US)

( * ) Notice: Subject to any disclaimer, the term of this patent is extended or adjusted under 35 U.S.C. 154(b) by 0 days.

(21) Appl. No.: 18/030,775

(22) PCT Filed: Oct. 8, 2021

(86) PCT No.: PCT/IB2021/059248
§ 371 (c)(1),
(2) Date: Apr. 7, 2023

(87) PCT Pub. No.: WO2022/074622
PCT Pub. Date: Apr. 14, 2022

(65) Prior Publication Data
US 2023/0271948 A1 Aug. 31, 2023

(30) Foreign Application Priority Data
Oct. 8, 2020 (EP) .................................. 20200872

(51) Int. Cl.
C07D 405/12 (2006.01)
A61K 8/67 (2006.01)
A61Q 19/08 (2006.01)

(52) U.S. Cl.
CPC ............ C07D 405/12 (2013.01); A61K 8/678 (2013.01); A61Q 19/08 (2013.01)

(58) Field of Classification Search
CPC .................................................. C07D 405/12
USPC ....................................................... 514/337
See application file for complete search history.

(56) References Cited

U.S. PATENT DOCUMENTS

| 5,217,992 A | 6/1993 | Wright et al. |
| 2008/0038316 A1 | 2/2008 | Wong et al. |
| 2012/0122969 A1* | 5/2012 | Miller ............... A61P 25/00 549/408 |

FOREIGN PATENT DOCUMENTS

| WO | 9619214 A1 | 6/1996 |
| WO | 2009003899 A1 | 1/2009 |
| WO | 2010126910 A1 | 11/2010 |
| WO | 2018136871 A1 | 7/2018 |

OTHER PUBLICATIONS

Karrer, Org. Chem. 2nd Ed. (1946), Elsevier Publishing Co., Inc. NY., 1946, pp. 91-102.*
Miller et al., J. Chromatography A, vol. 865 (1999) pp. 211-226.*
Lars Muller, et al., In vitro antioxidant activity of tocopherols and tocotrienols and comparison of vitamin E concentration and lipophilic antioxidant capacity in human plasma, Molecular Nutrition & Food Research, 2010, pp.731-742, vol. 54.
Yasukazu Yoshida, et al., Comparative study on the action of tocopherols and tocotrienols as antioxidant: chemical and physical effects, Chemistry and Physics of Lipids, 2003, pp. 63-75, vol. 123.
Miaomiao Guo, et al., Inhibitory effects of Schisandra chinensis extract on acne-related inflammation and UVB-induced photoaging, Pharmaceutical Biology, 2016, pp. 2987-2994, vol. 54, No. 12.
Akira Shibata, et al., Suppression of γ-Tocotrienol on UVB Induced Inflammation in HaCaT Keratinocytes and HR-1 Hairless Mice via Inflammatory Mediators Multiple Signaling, Journal of Agricultural and Food Chemistry, 2010, pp. 7013-7020, vol. 58, No. 11.
Maria Laura Colombo, An Update on Vitamin E, Tocopherol and Tocotrienol-Perspectives, Molecules, 2010, pp.2103-2113, vol. 15.
D. Manor, et al., The α-Tocopherol Transfer Protein, Vitamins and Hormones, 2007, pp. 45-48, 51-65, vol. 76.
Ping Tou Gee, Unleashing the untold and misunderstood observations on vitamin E, Genes & Nutrition, 2011, pp. 5-16, vol. 6.
R. M. Parkhurst, et al., Chromanols and Tocopherols, Chemistry of Heterocyclic Compounds, pp. 59-137, vol. 36.
E. Heymann, et al., Organophosphate Sensitive and Insensitive Carboxylesterases in Human Skin, Chem.-Biol. Interactions, 1993, pp. 217-226, vol. 87.
William Montagna, Histology and Cytochemistry of Human Skin, IX. The Distribution of Non-Specific Esterases, 1955, The Journal of Biophysical and Biochemical Cytology, pp. 13-16, vol. 1, No. 1.
Effat Khodaeiani, et al., Topical 4% nicotinamide vs. 1% clindamycin in moderate inflammatory acne vulgaris, International Journal of Dermatology, 2013, pp. 999-1004, vol. 52.
Frances M. Walocko, et al., The role of nicotinamide in acne treatment, Dermatologic Therapy, 2017, pp. 1-7, e12481.
Heidi M Rolfe, A review of nicotinamide: treatment of skin diseases and potential side effects, Journal of Cosmetic Dermatology, 2014, pp. 324-328, vol. 13.

* cited by examiner

Primary Examiner — Taofiq A Solola
(74) Attorney, Agent, or Firm — Bayramoglu Law Offices LLC

(57) ABSTRACT

The use of tocotrienols in medicine, veterinary or cosmetics, namely through the stabilization of tocotrienols, in particular in cosmetic formulations without hampering its functions in the skin is provided. In particular, the modification of tocotrienols with nicotinic acid results in the stabilization of the molecule and the penetration profile in human skin. The compounds and composition of are useful in medicine, veterinary or cosmetic industry namely in the prevention, therapy or treatment of skin diseases, skin disorders, or as a therapy or treatment of acne, seborrheic dermatitis or as an anti-aging agent.

14 Claims, 4 Drawing Sheets

TOCOTRIENOLS DERIVATES, METHODS AND USES THEREOF

CROSS REFERENCE TO RELATED APPLICATIONS

This application is the national stage entry of International Application No. PCT/I82021/059248 filed Oct. 8, 2021, and which is based upon and claims priority to European Patent Application No. 20200872.8 filed Oct. 8, 2020, the entire contents of which are incorporated by reference herein.

TECHNICAL FIELD

The present disclosure relates to the use of stabilized tocotrienols in the medical, veterinary, or cosmetic industry. In particular, the use of stabilized tocotrienols in the prevention, therapy, or treatment of skin diseases or disorders such as acne, seborrheic dermatitis, rosacea, or as an anti-aging agent.

BACKGROUND

Vitamin E refers to tocochromanols, a group of eight molecules with similar chemical structure: four tocopherols, each consisting of a saturated (phytyl) chain linked to a chromanol ring which differs in the level of methylation ($\alpha$, $\beta$, $\gamma$, $\delta$); and four tocotrienols, each consisting of an unsaturated (phytyl) side chain linked to a chromanol ring which differs in the level of methylation ($\alpha$, $\beta$, $\gamma$, $\delta$). Vitamin E occurs naturally in all plant species and in some cyanobacteria [1]. The concentration levels of each isomer depend on the organism, the plant species and the plant part (leaves, roots, seeds, etc.). Important sources of tocochromanols are palm oil, rice bran, and annatto oil.

Tocochromanols are powerful antioxidants. They are known as strong chain-breaking, peroxyl radical-scavenging antioxidants which are also able to quench singlet oxygen. When their antioxidant power is tested in solution or liposomal membranes, both tocopherols and tocotrienols show the same power in their corresponding isomers, but the antioxidant power between the various isomers falls according to the sequence $\alpha>\beta=\gamma>\delta$ [1]. It is suggested that tocotrienols, due to their unsaturated fatty acid chain, may present increased antioxidant power due to higher mobility in and between membranes, and less restricted interaction with lipid radicals. In addition, unlike tocopherols, tocotrienols do not increase membrane rigidity [2].

In addition to the antioxidant effect, vitamin E has been shown to also display anti-inflammatory [3], anti-tumor and anti-angiogenic effects. The anti-inflammatory effects come from the ability of these molecules to block the secretion of TNF-$\alpha$ and IL-1$\beta$, as well as the production of cytosolic cyclooxygenase-2 (COX-2) and inducible nitric oxide synthase (iNOS). All these biological factors impact greatly the inflammatory response cell-signaling cascade. It was also found that of all the isomers, the $\delta$-tocotrienol was the most effective for this purpose while also possessing the ability to block the lipopolysaccharide (LPS) induced gene expression of TNF-$\alpha$, IL-1$\beta$, IL-6 and iNOS [4].

In the skin, vitamin E acts as an antioxidant and anti-inflammatory, protecting from oxidative stress damage by scavenging for reactive oxygen species (ROS), such as peroxyl radicals and singlet oxygen, and by regenerating endogenous glutathione (GSH) to its reduced form. As compared to $\alpha$-tocopherol, tocotrienols have stronger antioxidant power and anti-inflammatory effects as they activate additional anti-inflammatory pathways. However, the natural delivery of tocotrienols has major drawbacks as they have low stability in their neat form and have poor bioavailability.

Tocochromanols, most commonly $\alpha$-tocopherol, are present in the human body, such as in cell membranes and plasma (on average, one low density lipoprotein (LDL) aggregate contains 5-12 $\alpha$-tocopherol molecules and less than one tocotrienol or other antioxidant molecules). Humans are unable to synthesize tocochromanol molecules and must acquire them through food sources; therefore, these are classified as essential nutrients [5].

The process of absorption of tocochromanols is facilitated by the assistance of $\alpha$-tocopherol transfer protein ($\alpha$-TTP); however, $\alpha$-TTP shows higher affinity for the alpha isomer of tocopherol, which partly explains the low oral bioavailability of the other isomers and forms of vitamin E [6].

Bioavailability and localization of vitamin E in the organism depends greatly on the path of administration. Oral administration is efficient for the delivery of vitamins to internal systems of the organism but is less efficient in the delivery of vitamin E to the outer layers of the skin where it is most needed in the treatment of topical conditions. This is due to the lipophilic nature and size of the molecule. Therefore, topical delivery is often preferred for the rapid renewal of vitamin E content in the skin.

Other than $\alpha$-tocopherol, the oral bioavailability of all other vitamin E isomers is substantially lower. A small quantity of isomers of tocotrienols bypass the $\alpha$-TTP by diffusion but are still present at very low concentrations in tissues. It has been shown that supplementation of $\alpha$-tocopherol greatly depresses the bioavailability and endogenous concentration of other vitamin E isomers (particularly tocotrienols) and decreases their associated superior effects [7].

When applied topically, vitamin E has a high affinity for the stratum corneum due to its lipophilic nature and has trouble penetrating deeper in the skin. Therefore, topically delivered vitamin E will have high residence time in the outer layer of the skin, where it is exposed to oxidative factors and can quickly degrade, thus losing function. This is an important limiting factor for topical applications, and it further decreases delivery efficiency.

The high degradation rate of tocochromanols is due to the antioxidant nature of these molecules, which causes them to promptly react with singlet oxygen or other ROS present in the atmosphere. Furthermore, the chroman ring, present in all the vitamin E isomers, is prone to UV degradation.

Many strategies have been developed to reduce degradation of vitamin E in cosmeceutical formulations. For example, inclusion of sacrificial co-antioxidants (like vitamin C), colloidal encapsulation systems or chemical modifications of the molecules.

Chemical modification is the most widely used strategy due to its simplicity and ease of obtaining modified vitamin E molecules which are able to circumvent both the skin penetration and molecular stability problems. These modifications usually target the hydroxyl group of the chroman ring, the easiest and most biologically sensible place to modify. A plethora of 0-modified tocopherols for the purpose of topical skin application have been created. Examples include tocopherol phosphate, tocopherol phosphate salt, tocopherol ascorbyl phosphate, tocopherol succinate, tocopherol acetate, tocopherol chloroacetate, tocopherol propionate, tocopherol amino acid salts, and tocopherol salicylate [8]. The most used in current formulations for the treatment of skin conditions are α-tocopherol acetate and α-tocopherol succinate.

The ester bond between α-tocopherol and the attached modifying compound is of particular importance. When modified in the hydroxyl group, vitamin E loses its antioxidant properties [1] but gains resistance to chemical degradation. The antioxidant power of vitamin E is achieved through the transference of radicals from ROS to the hydroxyl group, forming tocopheryl and/or tocotrienyl radicals which are more easily disposed of by endogenous metabolic processes.

The ester bond at the hydroxyl group is of particular interest because of the presence of enzymes such as non-specific esterases in the skin that hydrolyze the esterified tocopherol or tocotrienol, yielding the original neat tocopherol or tocotrienol and the original neat modifying compound. The hydrolyzed products maintain their normal chemical and biological activity. Activity of these non-specific esterases is not uniform throughout the skin, with higher activity being reported in several zones such as between the stratum corneum and the stratum granulosum, the outer sheath of active hair follicles, young sebaceous cells, and old accumulated sebum [9, 10]. The latter is of particular interest due to the accumulation of sebum in cases of acne. The ester modification is exceptionally stable in neutral formulations but will tend to degrade if the pH is too acidic or basic due to the inherent nature of esters. The chemical modification of tocochromanol molecules can enhance their penetration by modifying the molecules' polarity, allowing them to penetrate more easily into the stratum corneum.

When tocopherol and tocotrienol molecules modified through an ester bond are broken by the esterases, the modifying compound is also released into the skin, which is an important factor to take into account due to potential side effects, antagonism, synergy or cytotoxicity. The most common modifications in the market release compounds, such as acetate and succinate, that are used in regular metabolism, so as to decrease side effects as much as possible. However, using a modifying molecule that lacks therapeutic effects is a wasted opportunity to further increase the effectiveness of the formulation on the topical treatment by relying on multipronged or synergistic effects.

Vitamin B3, both in its amide (Niacinamide) or carboxylic acid (Nicotinic acid) form, is a precursor of essential coenzymes for numerous metabolic processes, such as cellular energy metabolism, regulation of DNA synthesis and transcription processes. Lower than normal levels of this vitamin can lead to pellagra, a condition characterized by photosensitive dermatitis, diarrhea and dementia [11, 12]. However, nowadays, it is a rare condition for someone with an average diet, since fish, meat and wheat are rich sources of this vitamin.

Vitamin B3 also possesses neuro-protective and antioxidant effects which reduce sebum production, wrinkles, ultraviolet induced immuno-suppression and skin pigmentation [12].

Cosmeceuticals with niacinamide or related compounds are effective for the treatment of skin conditions. However, niacinamide and its related compounds can cause side effects such as redness in the area applied, and systemic inflammation due to its high penetration ability which allows it to enter the bloodstream [13].

These facts are disclosed in order to illustrate the technical problem addressed by the present disclosure.

SUMMARY

The present disclosure relates to the use of stabilized tocotrienols in the medical, veterinary, or cosmetic industry. In particular, the use of stabilized tocotrienols in the prevention, therapy, or treatment of skin diseases or disorders such as acne, seborrheic dermatitis, rosacea, or as an anti-aging agent.

The present disclosure describes the modification of tocotrienols with nicotinic acid, the modification of tocotrienols with a linker and nicotinic acid or nicotinyl alcohol, the higher stability of the modified tocotrienols in cosmetic formulations, the penetration of modified tocotrienols into human skin, and the conversion of the modified tocotrienols into the original tocotrienol and nicotinic acid, thus allowing for effective and simultaneous topical delivery of tocotrienols and nicotinic acid.

Tocotrienols and tocopherols are part of the group of molecules collectively known as vitamin E and also referred to as "tocols". Nicotinic acid refers to vitamin B3, the precursor for niacinamide, which is involved in the synthesis of other important metabolic molecules.

In an embodiment, the combination of α-tocopherol with nicotinic acid is achieved through an ester bond produced from the reaction between the hydroxyl group of α-tocopherol and the carboxyl group of nicotinic acid. The molecule obtained is hereafter designated α-tocopheryl nicotinate.

In an embodiment, the combination of the different tocotrienols with nicotinic acid is achieved through an ester bond produced from the reaction between the hydroxyl group of tocotrienols and the carboxyl group of nicotinic acid. The molecules obtained from the combination of nicotinic acid with α-tocotrienol, γ-tocotrienol, and δ-tocotrienol are hereafter designated α-tocotrienyl nicotinate, γ-tocotrienyl nicotinate and δ-tocotrienyl nicotinate, respectively. Collectively they are designated as modified tocotrienols.

In an embodiment, the combination of α-tocotrienol with nicotinic acid or nicotinyl alcohol and another molecule in-between, hereafter referred to as "linker" or "linkers," is achieved through ester or amide bonds between the hydroxyl, amine and carboxyl groups of the various molecules involved in the reaction. The linkers used in this work are glycolic acid, ferulic acid, glycine, and succinic acid. The abovementioned linkers are examples used for illustration purposes; other linkers may be used in the reaction. The molecules obtained from the combination of nicotinic acid and glycolic acid, ferulic acid and glycine linkers with α-tocotrienol are hereafter designated α-tocotrienyl glycolyl nicotinate, α-tocotrienyl ferulyl nicotinate and α-tocotrienyl glycinyl nicotinate, respectively. The molecule obtained from the combination of nicotinyl alcohol and succinic acid linker with α-tocotrienol is hereafter designated α-tocotrienyl nicotinyl succinate. Collectively they are designated as modified α-tocotrienols with linkers.

In an embodiment, the modification of the other tocotrienol isomers (γ, δ) with a linker and nicotinic acid or nicotinyl alcohol can be obtained through the same synthetic routes by selecting any of the isomers, to obtain the respective modified tocotrienol with linker.

In an embodiment, the esterification of tocotrienols and nicotinic acid is achieved through 1-Ethyl-3-(3-dimethylaminopropyl)carbodiimide (EDC)/4-dimethylaminopyridine (DMAP) coupling reactions. The type of reaction and the reaction conditions selected are here described as an example of obtaining the modified tocotrienol molecules. The modified tocotrienol molecules were successfully synthetized and the structure and purity were confirmed by several analytical methods.

In an embodiment, the esterification of tocotrienols and nicotinic acid is achieved through acyl halide coupling reactions, specifically using nicotinoyl chloride. The type of reaction and the reaction conditions selected are here described as an example for obtaining the modified tocotrienol molecules. The modified tocotrienol molecules were successfully synthetized and the structure and purity were confirmed by several analytical methods.

In an embodiment, the esterification/amidation of α-tocotrienol, linker and nicotinic acid/nicotinyl alcohol is achieved through different synthetic routes specific for each compound.

In an embodiment, the synthesis of α-tocotrienyl glycolyl nicotinate and α-tocotrienyl ferulyl nicotinate comprises esterification of glycolic acid or ferulic acid and nicotinic acid through an acyl halide coupling reaction, specifically using nicotinoyl chloride, followed by an esterification of the resulting intermediate molecule with α-tocotrienol through EDC/DMAP coupling reactions.

In an embodiment, the synthesis of α-tocotrienyl glycinyl nicotinate comprises esterification of α-tocotrienol and BOC-Glycine-OH through an EDC/DMAP coupling reaction, followed by a deprotection of the obtained intermediate molecule through a selective hydrolysis of the BOC group using trifluoroacetic acid, followed by amidation of the obtained intermediate and nicotinic acid through an EDC/DMAP coupling reaction.

In an embodiment, the synthesis of α-tocotrienyl nicotinyl succinate comprises esterification of nicotinic acid and succinic acid through an acid catalyzed anhydride coupling reaction, specifically using sulfuric acid and succinic anhydride, followed by esterification of the resulting intermediate molecule with α-tocotrienol through an EDC/DMAP coupling reaction.

In an embodiment, the type of reaction and the reaction conditions selected serve as examples for obtaining the modified α-tocotrienols with linkers molecules.

In an embodiment, the structure and purity of the modified tocotrienols and modified α-tocotrienols with linkers obtained were confirmed by routine analytical methods.

In an embodiment, the penetration into human skin and the conversion of the modified tocotrienols and modified α-tocotrienols with linkers molecules in the human skin were evaluated by permeation experiments using Franz diffusion cells. The conversion profile was evaluated and quantified by measuring nicotinic acid or nicotinyl alcohol in the permeate solutions.

In an embodiment, the skin penetration and permeation of modified tocotrienols and modified α-tocotrienols with linkers molecules were compared with α-tocopheryl nicotinate.

In an embodiment, the penetration of modified tocotrienols and α-tocopheryl nicotinate was evaluated by quantifying the amount of non-modified molecules present inside the skin after defined time periods.

The experimental results have confirmed that modified tocotrienol molecules, modified α-tocotrienols with linkers and also α-tocopheryl nicotinate, penetrate into the skin and are converted back to the initial tocotrienol (or tocopherol), nicotinic acid and nicotinyl alcohol molecules. It was also found that the release rate of nicotinic acid differs for different modified tocotrienol molecules. The release of nicotinic acid from α-tocotrienyl nicotinate was three times faster than from γ-tocotrienyl nicotinate or δ-tocotrienyl nicotinate. The release of nicotinic acid from α-tocotrienyl nicotinate was also faster than from α-tocopheryl nicotinate.

In an embodiment, the chemical stability of α-tocopheryl nicotinate, the modified tocotrienols, some modified α-tocotrienols with linkers, non-modified tocotrienols and α-tocopherol in a cosmetic formulation was evaluated in accelerated aging tests (45° C.).

In an embodiment, the chemical stability of the modified tocotrienols, modified α-tocotrienols with linkers, α-tocopheryl nicotinate molecules and of α-tocopherol, α-tocotrienol, γ-tocotrienol, and δ-tocotrienol molecules were evaluated and compared. The modified and non-modified molecules were individually mixed in a cosmetic formulation and subjected to accelerated aging. The results have shown that, after 3 months in these conditions, the quantity of non-modified α-tocopherol, α-tocotrienol, γ-tocotrienol and δ-tocotrienol decreased by 50% or more, while the modified molecules remain at >95% of the initial mass. For the modified α-tocotrienols with linkers, the results have shown that α-tocotrienyl ferulyl nicotinate is not stable, degrading even in cold storage temperatures while α-tocotrienyl glycolyl nicotinate, α-tocotrienyl glycinyl nicotinate and α-tocotrienyl nicotinyl succinate remain at >95% of the initial mass. Therefore, with the exception of α-tocotrienyl ferulyl nicotinate, the modified molecules were shown to be very stable in the tested cosmetic formulation and, importantly, present higher stability than the non-modified tocols.

In an embodiment, the modified molecules were shown to penetrate the human skin and to be converted into the parent molecules. The α-tocotrienyl nicotinate, preferably α-tocotrienyl glycolyl nicotinate, is converted at a higher rate than the other modified tocotrienols.

Another aspect of the present disclosure relates to a pharmaceutical or cosmetic composition comprising at least one compound of the formula (I), (II) or (III) of the present disclosure in combination with at least one pharmaceutically or cosmetically acceptable excipient.

An aspect of the present disclosure relates to a compound of the following general formula (I)

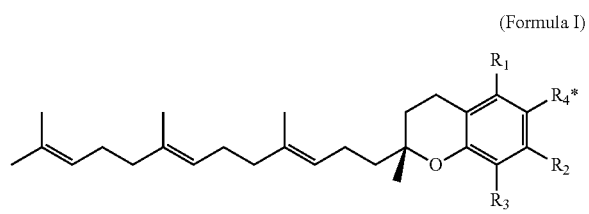

(Formula I)

wherein
$R_1$, $R_2$, $R_3$ and $R_4$ are independently selected from each other;
$R_1$ is H or $CH_3$;
$R_2$ is H or $CH_3$;
$R_3$ is H or $CH_3$;
$R_4$ is selected from a list consisting of

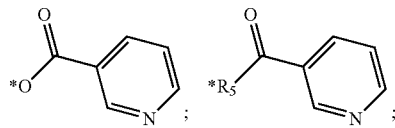

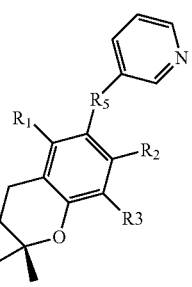

R₅ is a diester residue, or an amide ester residue, wherein * represents the binding site.

Preferably, the compound of the present disclosure may be used in medicine, more preferably the compound of the present disclosure may be used in the prevention, therapy or treatment of skin diseases, skin disorders, or as an anti-aging agent.

In an embodiment, R5 is a linker, preferably molecular residue of an appropriate linker that forms a diester or an ester and an amide when covalently linked to nicotinic acid (or nicotinoyl alcohol) or to the tocotrienol.

In an embodiment, the diester residue, or an amide ester residue (R5) is derived from any suitable, at least bifunctional molecule, in which at least one of the reactive groups is a carboxylic acid, via an adequate esterification reaction. The remaining functional groups must contain at least one reactive group chosen from: carboxylic (—COOH) acid group, hydroxyl (—OH) group or amine (—NH2) group.

In an embodiment, the compound of the following general formula (II):

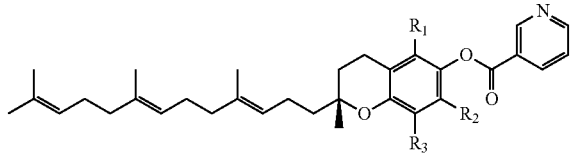

(Formula II)

wherein

R₁, R₂, R₃ are independently selected from each other;
R₁ is H or CH₃,
R₂ is H or CH₃,
R₃ is H or CH₃.

In an embodiment, the compound is formula (III)

(Formula III)

wherein

R₁, R₂, R₃ and R₅ are independently selected from each other;
R₁ is H or CH₃;
R₂ is H or CH₃;
R₃ is H or CH₃;
R₅ wherein R₅ is a diester residue, or an amide ester residue.

In an embodiment, R₅ is a glycolic diester residue, succinic diester residue, ferulic diester residue or glycine amide ester residue.

In an embodiment, the compound may be selected from the following molecules:

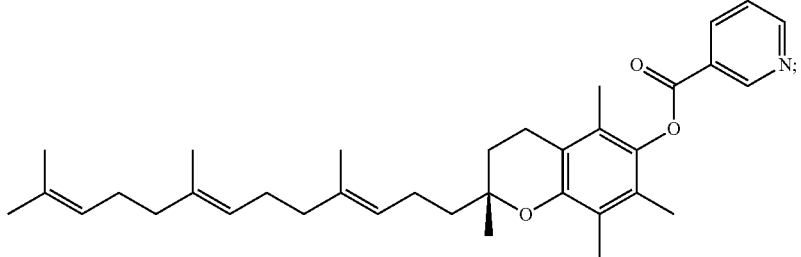

α-tocotrienyl nicotinate

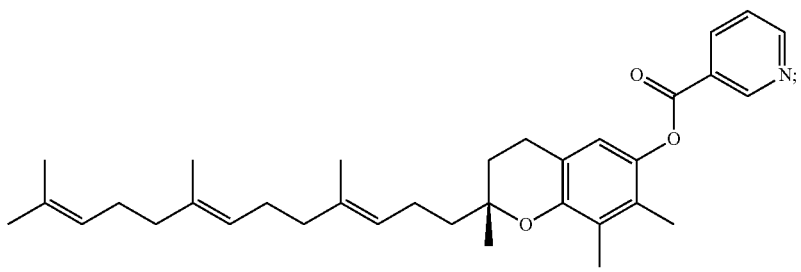

γ-tocotrienyl nicotinate

-continued
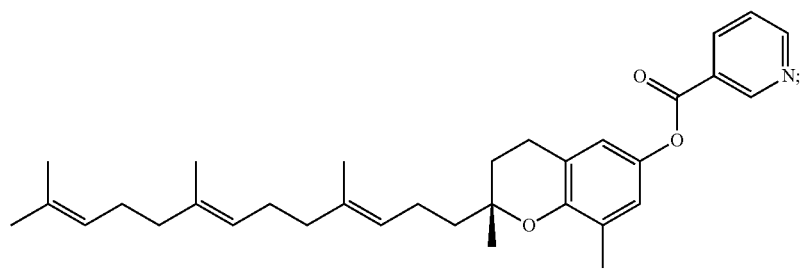
δ-tocotrienyl nicotinate
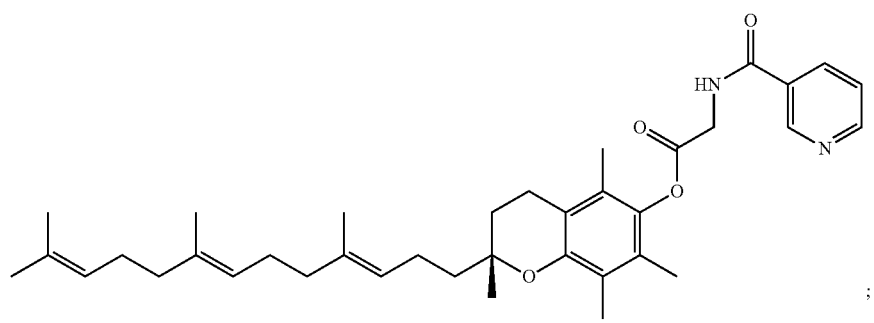
α-tocotrienyl glycinyl nicotinate
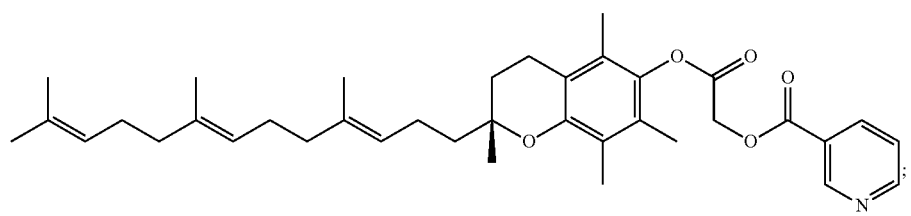
α-tocotrienyl glycolyl nicotinate
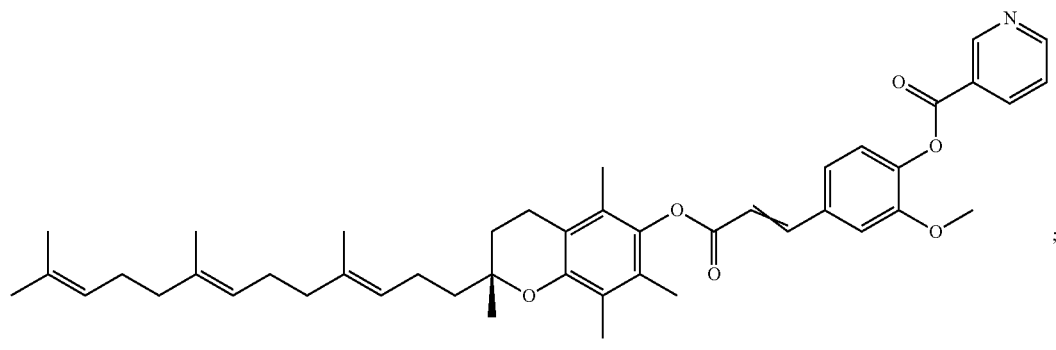
α-tocotrienyl ferulyl nicotinate
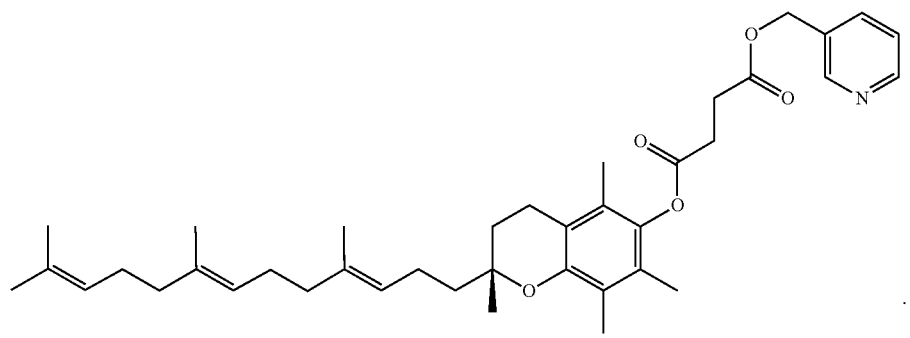
α-tocotrienyl nicotinyl succinate In an embodiment, the compound of the present disclosure may be used in medicine, veterinary or as a cosmetic. Namely, for use in prevention, therapy or treatment of skin diseases, skin disorders, or anti-aging. Preferably for the prevention, therapy or treatment of skin inflammation diseases. More preferably, for use in the prevention, therapy or treatment of acne or seborrheic dermatitis.

In an embodiment, the pharmaceutical or cosmetic composition of the present disclosure may comprise up to 20% by mass of at least one compound of the formula (I) compared to the total mass of the composition.

In an embodiment, the composition may comprise 0.01% to 10% by mass of at least one compound of the formula (I) compared to the total mass of the composition, more preferably 0.1% to 5% by mass of at least one compound of the formula (I) compared to the total mass of the composition, even more preferably 0.1% to 2% by mass of at least one compound of the formula (I) compared to the total mass of the composition.

Another aspect of the present disclosure relates to a method for prevention, therapy or treatment of acne, rosacea or seborrheic dermatitis, comprising the application on the skin of a compound, cosmetic/pharmaceutical composition and/or patch of the present subject matter.

In an embodiment, the composition may be a topical composition. Preferably, the topical composition is a gel, a cream, a lotion, an ointment, a serum, a paste, a foam, among others.

It is also disclosed a method for the cosmetic treatment of acne or seborrheic dermatitis comprising the application on the skin of a cosmetic/pharmaceutical composition.

BRIEF DESCRIPTION OF THE DRAWINGS

The following figures provide preferred embodiments for illustrating the description and should not be seen as limiting the scope of invention.

FIG. 4-4B: FIG. 4B—Side by side comparison of the concentration of nicotinic acid in the final permeation solution, after 48 hours for α-tocopheryl nicotinate (α-T-N), α-tocotrienyl nicotinate (α-T3-N), γ-tocotrienyl nicotinate (γ-T3-N), α-tocotrienyl ferulyl nicotinate (N-Fer-T3), α-tocotrienyl glycinyl nicotinate (N-Gly-T3), α-tocotrienyl glycolyl nicotinate (N-Glc-T3), and α-tocotrienyl nicotinyl succinate (N-Suc-T3) at 10% m/m.

DETAILED DESCRIPTION OF THE INVENTION

The present disclosure is also further described, in particular, using embodiments of the disclosure. Therefore, the disclosure is not limited to the descriptions and illustrations provided. These are used so that the disclosure is sufficiently detailed and comprehensive. Moreover, the intention of the drawings is for illustrative purposes and not for the purpose of limitation.

The present disclosure relates to an embodiment for the use of tocotrienols in medicine, veterinary or cosmetics, namely through the stabilization of tocotrienols, in particular in cosmetic formulations without hampering its functions in the skin. In particular, the present disclosure relates to the modification of tocotrienols with nicotinic acid, the stabilization of the molecule and the penetration profile in human skin.

The compounds and composition of the present subject matter are useful in medicine, veterinary or cosmetic industry namely in the prevention, therapy or treatment of skin diseases, skin disorders, or as a therapy or treatment of acne, seborrheic dermatitis or as an anti-aging agent.

Figure 1:
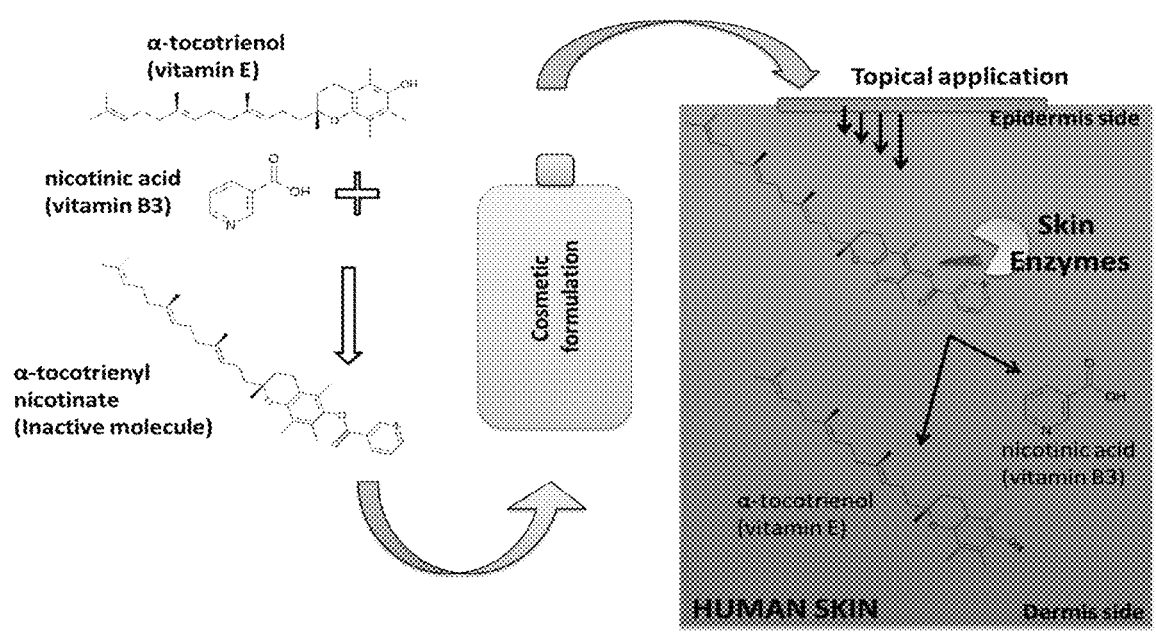
FIG. 1: Schematic representation of the modified tocotrienol, incorporation in a cosmetic formulation, penetration into human skin, and conversion to the parent molecules.

In an embodiment, α-tocopherol, α-tocotrienol, γ-tocotrienol or δ-tocotrienol were reacted with nicotinic acid following the procedure described in the general procedure. (FIG. 1)

In an embodiment, tocotrienols and tocopherol modification was performed by EDC/DMAP coupling. The evolution of the reactions was monitored by thin layer chromatography (TLC) and the products recovered after liquid-liquid extraction followed by purification by column chromatography. The structure of the new molecules and purity was confirmed by proton nuclear magnetic resonance (H-NMR), mass spectroscopy (MS), Fourier transformed infrared spectroscopy (FTIR) and high-performance liquid chromatography (HPLC).

In an embodiment, the modification of tocotrienols and tocopherol with nicotinic acid was achieved with a reaction procedure based on the coupling agent EDC and catalyzed by DMAP.

In an embodiment, EDC (1 mol eq.) and DMAP (0.05 mol eq.) are added to dichloromethane (DCM) and stirred at room temperature until complete dissolution (approximately 20 minutes is usually sufficient). This solution is then cooled to ≈0° C. with the help of an ice water bath and the nicotinic acid mass (1 mol eq.) is added until complete dissolution is observed. Then, the mass of tocotrienol or tocopherol, previously dissolved in DCM for ease of handling, is added to the reaction mixture followed by the immediate addition of N,N-diisopropylethylamine (DIEA) (1 mol eq.). The reaction mixture is then maintained under stirring overnight. The successful formation of the desired product(s) is monitored by TLC analysis.

In an embodiment, the reaction products obtained were purified. After the defined reaction time, the reaction mixture is extracted by liquid-liquid extraction with water to eliminate part of the non-reacted reagents and undesired side products that are water soluble. The evolution of the extractions is monitored by TLC.

In an embodiment, the organic fraction is then dried of residual water with anhydrous sodium sulphate, evaporated to eliminate the solvent. The solid residue is recovered and further purified by Normal Phase Column Flash Chromatography. The fractions collected are analyzed by TLC and combined accordingly. The solvent is then removed under vacuum on a rotatory evaporator, followed by overnight drying in a high vacuum chamber.

In an embodiment, the synthesis of α-tocotrienyl nicotinate was performed using nicotinic acid, EDC, DIEA and DMAP. The quantity of nicotinic acid, EDC, DIEA and DMAP used are in excess relative to α-tocotrienol. In a procedure, 1745 mg of α-tocotrienol and 1251 mg of nicotinic acid were reacted using 4164 mg of EDC, 1745 μL of DIEA and 85 mg of DMAP in 30 mL of DCM. The purification of α-tocotrienyl nicotinate was performed by column chromatography, with silica gel 60 and elution with DCM/methanol 40:1.

In an embodiment, the synthesis of γ-tocotrienyl nicotinate was performed using nicotinic acid, EDC, DIEA and DMAP. The quantity of nicotinic acid, EDC, DIEA and DMAP used are in excess relative to γ-tocotrienol. In a procedure, 1326 mg of γ-tocotrienol and 985 mg of nicotinic acid were reacted using 2160 mg of EDC, 1380 μL of DIEA and 85 mg of DMAP in 30 mL of DCM. The purification of γ-tocotrienyl nicotinate was performed by column chromatography, with silica gel 60 and elution with DCM/methanol 40:1.

In an embodiment, the synthesis of δ-tocotrienyl nicotinate was performed using nicotinic acid, EDC, DIEA and DMAP. The quantity of nicotinic acid, EDC, DIEA and DMAP used are in excess relative to δ-tocotrienol. In a procedure, 584 mg of δ-tocotrienol and 566 mg of nicotinic acid were reacted using 1607 mg of EDC, 778 μL of DIEA and 53.2 mg of DMAP in 30 mL of DCM. The purification of δ-tocotrienyl nicotinate was performed by column chromatography, with silica gel 60 and elution with DCM/methanol 30:1.

In an embodiment the synthesis of modified α-tocotrienols with linkers was performed using a plethora of different synthetic routes according to the practical needs and considerations of each specific molecule.

In an embodiment, the evolution of the reactions was monitored by TLC.

In an embodiment, the structure and purity of the new molecules was confirmed by H-NMR, MS, FTIR and HPLC.

In an embodiment, the synthesis of α-tocotrienyl glycolyl nicotinate was performed in a two-step method. The first step is the esterification of glycolic acid and nicotinic acid, as follows: to a round bottom flask were added 500 mg of nicotinoyl chloride hydrochloride, 640 mg (3 eq.) of glycolic acid and 20 mL of acetonitrile, under stirring in an ethanolic ice bath; the mixture was stirred until the temperature of −10° C. was reached and upon which 1 mL of DIEA was added and the mixture was left to react for 1 hour. After the allotted reaction time 2.5 mL of palmitoyl chloride were added to the reaction medium, immediately followed by the addition of 2 mL of DIEA. The mixture was left to react for an additional 30 minutes. 10 mL of deionized water was then added to the reaction medium and the medium was stirred overnight; the reaction medium was then filtered, and the filtrate recovered. Acetonitrile in the filtrate was removed in vacuo in a rotary evaporator at about 45° C. and then freeze-dried to remove the remaining water. In the second step, the crude obtained by the first step was used without further purification. 400 mg of crude, 540 mg (6 eq.) of EDC, 5 mg of DMAP and 20 mL of DCM were mixed in a round bottom flask under stirring. 200 mg of α-tocotrienol dissolved in 0.5 mL of DCM were added to the mixture, followed by 0.5 mL of DIEA. The reaction was left stirring for 1 hour at a temperature ranging from 18° C. to 25° C. The reaction medium was successively extracted with 30 mL of 5% citric acid and three portions of 50 mL of deionized water. Organic fractions were recovered, combined, dried over sodium sulfate and filtered. Solvent was removed in vacuo in a rotary evaporator at about 45° C. The structure and purity of the new molecules were confirmed by H-NMR, MS, FTIR and HPLC.

In an embodiment, the synthesis of α-tocotrienyl ferulyl nicotinate was performed in a two-step method. In the first step, 720 mg (1.5 eq) of ferulic acid were dissolved in 20 mL of acetonitrile in a round bottom flask and cooled to −10° C. using an ethanolic ice bath. 980 mg of nicotinoyl chloride hydrochloride was added to the reaction vessel and the mixture was stirred for 5 minutes, followed by dropwise addition of 2 mL of DIEA under vigorous stirring over 1 minute. The reaction was stirred for a further 2 hours to ensure reaction completeness. The reaction medium was then successively extracted with three portions of 50 mL of deionized water; organic fractions were recovered, combined and dried over sodium sulfate. Solvent was then removed in vacuo in a rotary evaporator at about 30° C. The obtained crude was re-dissolved in a minimal amount of 5% formic acid in acetonitrile and purified by preparative HPLC in a reverse phase system (Waters Atlantis C18 Preparative column, 19×250 mm 10 μm, 60:40 acetonitrile:water at 20 mL/min). For the second step, 50 mg of the intermediate obtained from the first step were added to a round bottom flask, along with 96 mg of EDC (3 eq.) and 5 mg of DMAP in 10 mL of DCM and stirred thoroughly for 10 minutes. 70 mg of α-tocotrienol dissolved in 5 mL of DCM for ease of handling was added to the reaction vessel, immediately followed by the addition of 0.2 mL of DIEA, under vigorous stirring. The reaction was stirred for 2 hours to ensure completion. The reaction medium was then successively extracted with 30 mL of 5% (w/v) citric acid solution and three portions of 50 mL of deionized water. Organic fractions were combined and dried over sodium sulfate. Solvent was removed in vacuo in a rotary evaporator at about 30° C. The obtained crude was re-dissolved in a minimal amount of 5% formic acid in acetonitrile and purified by preparative HPLC in a reverse phase system (Waters Atlantis C18 Preparative column, 19×250 mm 10 μm, 100% acetonitrile at 20 mL/min).

In an embodiment, the synthesis of α-tocotrienyl glycinyl nicotinate was performed in a three-step method. In the first step were added to a round bottom flask 120 mg of BOC-Glycine-OH (1.5 eq.), 410 mg of EDC (4.5 eq.), 20 mg of DMAP and 15 mL of DCM under vigorous stirring. 120 mg of α-tocotrienol was dissolved in 5 mL of DCM, for ease of handling, and added to the reaction vessel, immediately followed by 3 mL of DIEA, under vigorous stirring. Reaction was stirred for a further 2 hours to ensure completion. Reaction medium was successively extracted with 30 mL of 5% citric acid in water and two portions of 50 mL of deionized water. Organic fractions were recovered, combined and dried over sodium sulfate. Solvent was removed in vacuo in a rotary evaporator at about 40° C. Crude was used in the following steps without further purification. In the second step a solution comprising 3 mL of DCM+3 mL of trifluoroacetic acid (TFA) was added to the crude under stirring and was left to react for 1 hour to ensure the removal of the BOC protecting group. Reaction medium was azeotropically evaporated with methanol in vacuo in a rotary evaporator at about 40° C. Crude was re-dissolved in DCM and extracted with three portions of 50 mL of deionized water. Organic fractions were recovered, combined, dried under sodium sulfate and filtered. In the third step the filtered organic fraction of the second step was placed in a round bottom flask under vigorous stirring and to it was added a previously prepared fresh solution of 120 mg of nicotinic acid (2 eq.), 1.2 g of EDC (6 eq.) and 5 mg of DMAP in 5 mL of DCM and stirred for a further 10 minutes. 1 mL of DIEA was added to the reaction medium and the reaction was stirred for a further 1 hour at room temperature to ensure completion. The reaction was successively extracted with 30 mL of 5% citric acid and three portions of 50 mL of deionized water. Organic fractions were recovered, combined and dried over sodium sulfate. Solvent was removed in vacuo in a rotary evaporator at about 40° C. The obtained crude was re-dissolved in a minimal amount of DCM and purified by Normal Phase Flash Chromatography. The column was packed with 50 g of silica gel 60 dispersed in a solution of 10:1 DCM:methanol, loaded with the full amount of crude obtained in the third step and eluted with a solution of 10:1 DCM:methanol.

In an embodiment, the synthesis of α-tocotrienyl nicotinyl succinate was performed in a two-step method. In the first step, 770 mg of succinic anhydride, 1.9 g of nicotinyl alcohol (1.9 eq.) and 20 mL of acetonitrile were added to a round bottom flask and stirred for 10 minutes. 200 μL of sulfuric acid 98% were then added to the mixture under vigorous stirring and the reaction was stirred for further 1 hour to ensure reaction completeness, though the reaction evolves quickly, forming clumps of a white and pale-yellow precipitates. The reaction medium was filtered, and filtrate was recovered and transferred to a round bottom flask under stirring. 4 mL of palmitoyl chloride and 2.5 mL of DIEA were added to the reaction vessel and the mixture was stirred for a further 1 hour. The reaction medium was again filtered, and the filtrate recovered. The filtrate was then extracted with three portions of 30 mL of hexane. Acetonitrile fraction was recovered, and solvent was removed in vacuo in a rotary evaporator at about 40° C. The crude obtained was dissolved in 50 mL of deionized water and filtered through a sintered glass filter (Size 4). The filtrate was recovered, freeze-dried and used for the following step without further purification. In the second step, 296 mg of the crude obtained in the previous step, 542 mg of EDC (6 eq.) and 20 mg of DMAP in 15 mL of DCM were mixed in a round bottom flask. 200 mg of α-tocotrienol dissolved in 5 mL of DCM were then added to the reaction medium, immediately followed by the addition of 4 mL of DIEA, under vigorous stirring. The reaction was stirred for a further 2 hours to ensure completion. The reaction was then successively extracted with a 5% citric acid solution and three portions of 50 mL of deionized water. The organic fractions were recovered, combined and dried with sodium sulfate. Solvent was removed in vacuo in a rotary evaporator at about 40° C. The obtained crude was dissolved in a minimal amount of 5% formic acid in acetonitrile and purified by preparative HPLC in a reverse phase system (Waters Atlantis C18 Preparative column, 19×250 mm 10 μm, 100% acetonitrile at 20 mL/min).

In an embodiment, TLC analyses were performed on aluminum backed silica gel 60 plates impregnated with fluorescence probe F254 (Merck). Plates were 8 cm in length, with 7.5 cm of run length for the samples. The developed plates were visualized under UV light (254 nm and 365 nm) before any developing solution (stain) was applied. The stains (TLC stains, Seebach's stain, Draggendorff stain) used are for the universal identification of compounds and also for the selective detection of compounds.

In an embodiment, the reaction products were further characterized by FTIR, HPLC, MS and H-NMR. The FTIR measurements were performed on an IRPrestige-21 Spectrophotometer from Shimadzu, using compressed potassium bromide (KBr) pellet windows. The spectra were obtained in the transmission mode, in the range of 4000 $cm^{-1}$ to 400 $cm^{-1}$, with resolution of 4 $cm^{-1}$ and as the average of 32 individual measurements. The HPLC analyses were performed on a Knauer chromatograph composed of 3 modules: Smartline manager 5000, Smartline pump 1000 and Smartline UV Detector 2600. The UV detector is fitted with a photodiode array (PDA) which allows for the continuous monitoring from 190-450 nm. The column system was composed of a pre-column (Reverse phase C18 Atlantis T3 5 μm, 4.6×20 mm) and a column (Reverse phase C18 Atlantis T3 5 μm, 4.6×250 mm), which were maintained at 30° C. using a dedicated oven. The elution was performed with acetonitrile (containing 0.1% v/v acetic acid) at 1 mL/min and the injection volume was 50 μL. The MS spectra were acquired on a Triple Quadruple Quattro Micro Mass spectrometer (Waters) by direct infusion of solutions containing the sample. The desolvation temperatures and gas flow (N2) were set to 300° C. and 600 L/h for the probe and 120° C. and 20 L/h for the capillary. The capillary voltage was 4.00 keV and the cone voltage was set to 40 V. The spectra were recorded in the daughter mode using argon (Ar) as collision gas. After selection and locking on the respective molecular ion m/z and adjustment of collision energy, the recordings were done in the m/z range of 50 to 600. The molecule of interest was dissolved in acetonitrile: methanol 1:1 and infused at 20 μL/min.

Figure 2:
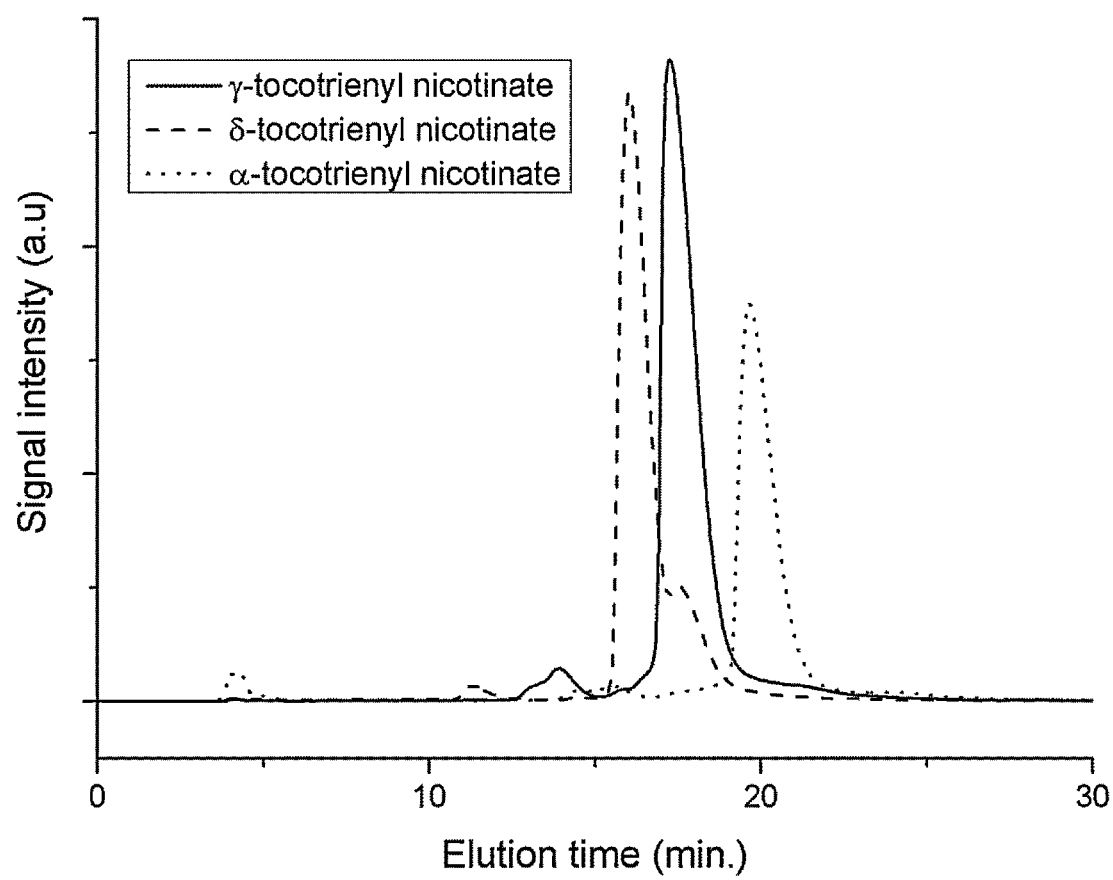
FIG. 2: Chromatograms of α-tocotrienyl nicotinate, γ-tocotrienyl nicotinate and δ-tocotrienyl nicotinate after the synthesis and purification process.

In an embodiment, after complete solvent removal, the modified molecules were further characterized following the protocols described. The FTIR results show the presence of a strong absorption band at approximately 1740 $cm^{-1}$, characteristic from the ester bond and the absence of absorption bands in the region of 2750-3500 $cm^{-1}$, characteristic of hydroxyl and carboxyl groups. The HPLC chromatograms (FIG. 2) for each purified reaction product present only one peak and the MS spectra show the presence of the expected molecular ion peak (according to Table I). The H-NMR spectra peaks are according with the expected structures. The modified tocotrienol and modified α-tocotrienols with linkers molecules were obtained with purity of 97% m/m or higher.

TABLE I

Result of MS analysis of reaction products - theoretical molecular mass and molecular ion peak obtained for synthesized molecules.

| Molecule | Theoretical Mass | Molecular Peak, [M + H]+ |
| --- | --- | --- |
| α-tocopherol | 430.71 | 431.24 |
| α-tocotrienol | 424.66 | 425.16 |
| γ-tocotrienol | 410.63 | 411.41 |
| δ-tocotrienol | 396.61 | 397.13 |
| α-tocopheryl nicotinate | 535.82 | 536.24 |
| α-tocotrienyl nicotinate | 529.77 | 531.25 |
| γ-tocotrienyl nicotinate | 515.74 | 516.40 |
| δ-tocotrienyl nicotinate | 501.72 | 502.31 |
| α-tocotrienyl glycolyl nicotinate | 587.80 | 588.11 |
| α-tocotrienyl ferulyl nicotinate | 705.94 | 706.24 |
| α-tocotrienyl glycinyl nicotinate | 586.82 | 587.11 |
| α-tocotrienyl nicotinyl succinate | 615.86 | 616.97 |

In an embodiment, the skin permeation of the modified compounds was assessed. The permeation tests were performed with full thickness human skin. These samples were obtained at a local hospital, from healthy donors undergoing cosmetic surgery. The excised skin was stored in a PBS solution containing 10% antibiotic and maintained at 4° C., until further processing in the laboratory. When the skin sample was received, the underlying fat tissue was removed and discarded. The remaining skin (dermis and epidermis layers) was cut into pieces of approximately 1.5×1.5 cm. When the permeation experiments were executed with fresh skin, the samples were immediately used. Otherwise, the pre-cut skin samples were frozen at −80° C. and stored for further use. When reclaiming the frozen skin samples, the samples were removed from storage and thawed to room temperature for 1 hour before further manipulation.

Figure 3:
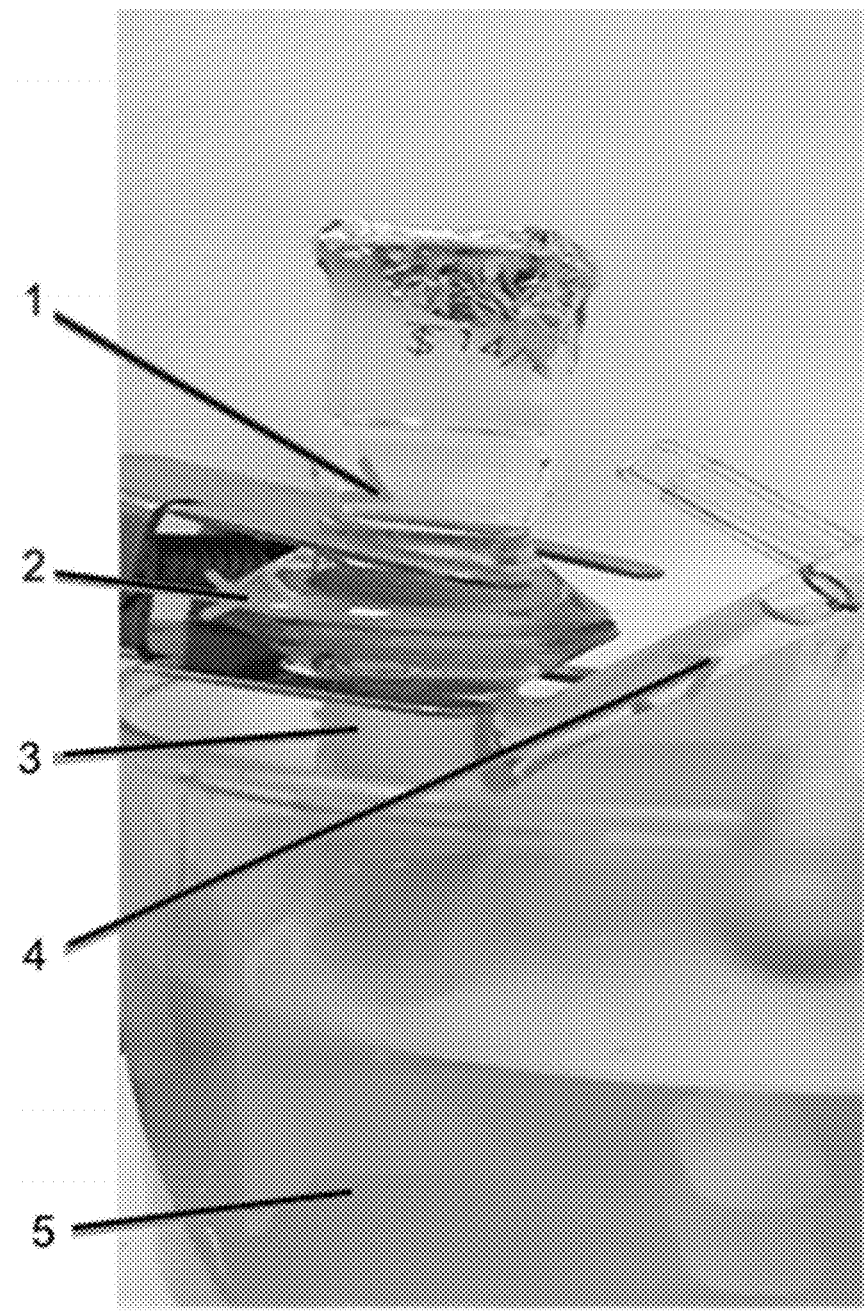
FIG. 3: Picture of a Franz diffusion cell used in permeation experiments. 1—Donor compartment; 2—Skin sample; 3—Receptor compartment; 4—Sampling access; 5—Thermostatic water bath.

The permeation experiments were performed in Franz diffusion cells. These diffusion cells are constituted by a donor compartment, where the formulation containing the permeate molecule is placed, and a receptor compartment containing the receptor fluid where the permeate molecule is collected and accumulated in time. The skin sample is placed between the donor and receptor compartments and is also equipped with a sampling access that allows for the collection of samples (a certain volume of the receptor fluid) without requiring the disassembly of the cell and therefore allows for the permeation experiment to continue (FIG. 3).

At the start of the experiment, the receptor compartment is filled with the receptor fluid, the skin sample is placed in place with care so as to not form air bubbles underneath. The donor receptor is positioned in place and clamped. The assembly is then placed in the thermostatic (37° C.) bath for 30 min to allow temperature equilibration. After the equilibration time, the level of the receptor fluid is adjusted as necessary. The receptor compartment is equipped with a magnetic mixer, ensuring the solution homogeneity during the course of the permeation experiment.

In an embodiment, the permeate solutions are monitored for the presence of nicotinic acid released from the modified tocopherol and tocotrienols molecules. The amount of nicotinic acid is quantified by HPLC using an ion pairing method. The concentration of nicotinic acid is calculated from a standard calibration curve of known nicotinic acid concentration solutions measured in the same conditions. The HPLC analysis is performed on a Knauer chromatograph consisting of 3 modules: Smartline manager 5000, Smartline pump 1000 and Smartline UV Detector 2600. The UV detector is fitted with a photodiode array (PDA) which allows for the continuous monitoring from 190-450 nm. The online chromatograms are monitored at 254 nm. The eluent comprises an ion-pairing eluent (50 mM of tetrabutylammonium hydroxide (TBAOH), pH corrected to 7.4 with hydrogenphosphate dibasic ($Na_2H_2PO_4$)) containing 10% of acetonitrile at a flow of 1 mL/min and the column used is an Atlantis T3 4.6×250 mm (with guard column of same type 4.6×20 mm) at 30° C.

Figure 4A:
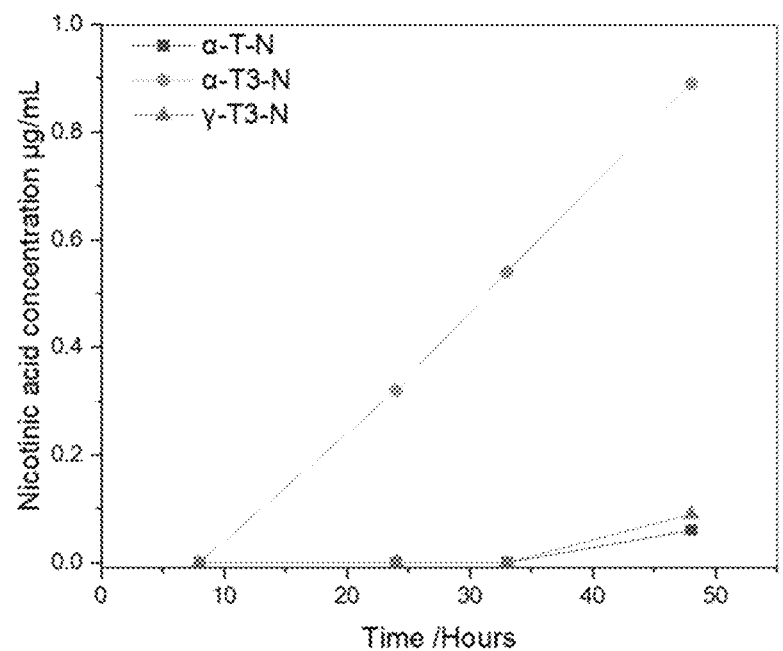
FIG. 4A—Evolution of the concentration of nicotinic acid in the permeate solution with time of permeation for α-tocopheryl nicotinate; α-tocotrienyl nicotinate and γ-tocotrienyl nicotinate at 5% m/m.
Figure 4B:
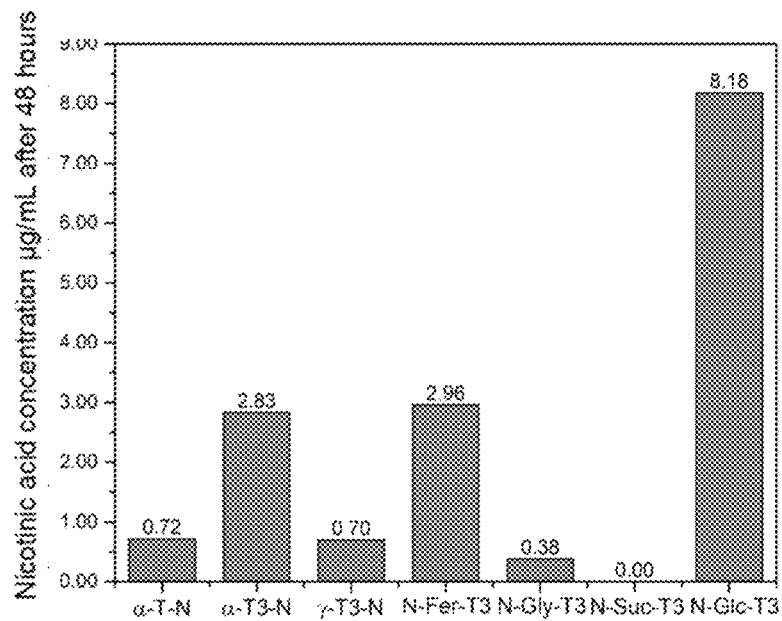

In an embodiment, the skin permeation experiments are performed with formulations of different concentrations of modified tocotrienol and tocopherol molecules. The modified molecules are dissolved at concentrations of 5% and 10% m/m in a mixture of equal volumes of 2-(2-ethoxyethoxy)ethanol and propylene glycol and 150 µl of these solutions are applied on the skin samples. The concentration of nicotinic acid present in the permeate solutions of the experiment with a donor solution of concentration of 5% m/m is quantified for different time points (8, 24, 33 and 48 h). For the experiment with a donor solution of concentration of 10% m/m, the concentration of nicotinic acid in the permeate solutions is quantified after 48 hours of permeation. The results obtained are expressed in Table II and FIG. 4.

TABLE II

Concentration (µg/ml) of nicotinic acid in the permeate solution.

| Concentration | Time Point/ Hours | Permeating Compound | | |
|---|---|---|---|---|
| | | α-T-N | α-T3-N | γ-T3-N |
| 5% m/m | 8 | ND | ND | ND |
| | 24 | ND | 0.32 | ND |

TABLE II-continued

Concentration (µg/ml) of nicotinic acid in the permeate solution.

| Concentration | Time Point/ Hours | Permeating Compound | | |
|---|---|---|---|---|
| | | α-T-N | α-T3-N | γ-T3-N |
| | 33 | ND | 0.54 | ND |
| | 48 | 0.06 | 0.89 | 0.09 |
| 10% m/m | 48 | 0.72 | 2.83 | 0.70 |

α-T-N: α-tocopheryl nicotinate;
α-T3-N: α-tocotrienyl nicotinate;
γ-T3-N: γ-tocotrienyl nicotinate;
ND: Non-detectable.

In an embodiment, the skin permeation experiments were performed with formulations of different concentrations of modified α-tocotrienol with linkers molecules. The modified molecules were dissolved at concentrations of 10% m/m in a mixture of equal volumes of 2-(2-ethoxyethoxy)ethanol and propylene glycol and 150 µL of these solutions applied on the skin samples. The concentration of nicotinic acid in the permeate solutions from the experiments with α-tocotrienyl ferulyl nicotinate, α-tocotrienyl glycolyl nicotinate, and α-tocotrienyl glycinyl nicotinate was quantified by HPLC using the ion pairing method described. The concentration of nicotinyl alcohol in the permeate solution from α-tocotrienyl nicotinyl succinate was measured by HPLC, using the same system configuration, but using water as eluent. The concentrations of nicotinic acid and nicotinyl alcohol were determined after 24 and 48 hours of permeation. The results obtained are expressed in Table III.

TABLE III

Concentration (µg/mL) of nicotinic acid and nicotinyl alcohol in the permeate solution.

| Concentration | Time Point/ Hours | Permeating Compound | | | |
|---|---|---|---|---|---|
| | | N-Fer-T3 | N-Gly-T3 | N-Suc-T3 | N-Glc-T3 |
| 10% m/m | 24 | 1.19 | 0.18 | NQ* | 3.02 |
| | 48 | 2.96 | 0.38 | | 8.18 |

N-Fer-T3: α-tocotrienyl ferulyl nicotinate;
N-Gly-T3: α-tocotrienyl glycinyl nicotinate;
N-Suc-T3: α-tocotrienyl nicotinyl succinate;
N-Glc-T3: α-tocotrienyl glycolyl nicotinate;
NQ: Non-quantifiable.
*Trace amounts of nicotinyl alcohol detected, insufficient for quantification.

In an embodiment, the amount of modified tocotrienol or modified tocopherol compound present inside the skin was quantified at the end of the permeation experiment. For this purpose, at the end of the permeation experiment with a donor solution of concentration of 10% m/m, the skin samples were collected, the remaining formulation present in the donor compartment of the Franz diffusion cell was removed and washed thoroughly with distilled water. The skin samples were extracted with three volumes of 5 mL of acetonitrile, the volumes combined, and the presence of modified compounds quantified by HPLC following the analytical conditions described for determination of the compounds' purities. The amount of modified compound was found to be comparable between the different molecules and approximately 0.600 mg/cm$^2$ of skin.

In an embodiment, the highest level of nicotinic acid was found in the permeate solutions of α-tocotrienyl nicotinate for molecules without a linker, and for α-tocotrienyl glycolyl nicotinate for molecules with a linker.

In an embodiment, the chemical stability of the modified molecules was evaluated in accelerated degradation tests. For this purpose, the test molecules were formulated in a cosmetic relevant formulation and its degradations were assessed for a period of 3 months.

In an embodiment, the cosmetic formulation may comprise water, jojoba seed oil, butylene glycol, squalane, sodium hyaluronate, cetearyl alcohol and a carbomer.

In an embodiment, the cosmetic formulation may comprise further ingredients suitable for obtaining further desired characteristics in the cosmetic formulation.

In an embodiment, test molecules were added to the cosmetic formulation at 0.1% m/m level, thoroughly homogenized to ensure uniform dispersion and stored in closed glass bottles in an oven at 45° C. for 3 months. In order to evaluate homogeneity and stability, 3 samples were collected from random positions immediately after preparation and at each time point evaluated. The quantification of the test molecules was performed by HPLC.

In an embodiment, the preparation of the mixtures for evaluation of the stability was performed according to the following experimental protocol. The mass of compound was weighed and dissolved in 2-(2-ethoxyethoxy)ethanol (also weighed) and added to a known mass of moisturizer product. The mixture was homogenized, and 3 samples were collected to confirm homogenous distribution and initial concentration of modified molecules. The mixtures were then stored in an oven at 45° C. for 3 months (Table IV).

In an embodiment, the stability of the test molecules in the cosmetic formulation was determined. The test mixtures were sampled in triplicate from random zones. The samples were prepared for analysis by solubilizing them in acetonitrile and the quantification of the modified and non-modified tocopherol and tocotrienol molecules was performed by HPLC. The % of the initial compounds is described in Table IV. The modified tocotrienols did not degrade during the storage time while the non-modified tocotrienols degraded to about half or less of the initial quantity. The modified α-tocotrienols with linkers showed different behavior depending on the molecule. α-tocotrienyl glycinyl nicotinate, α-tocotrienyl glycolyl nicotinate and α-tocotrienyl nicotinyl succinate showed excellent stability, while α-tocotrienyl ferulyl nicotinate is unstable even in cold storage conditions.

TABLE IV

% of initial compound after stored in an oven at 45° C. for 3 months.

| Compound | % of the Compound after 3 Months |
|---|---|
| α-tocopherol | 44% |
| α-tocotrienol | 53% |
| γ-tocotrienol | 20% |
| δ-tocotrienol | 57% |
| α-tocopheryl nicotinate | ≥95% |
| α-tocotrienyl nicotinate | ≥95% |
| γ-tocotrienyl nicotinate | ≥95% |
| δ-tocotrienyl nicotinate | ≥95% |
| α-tocotrienyl glycinyl nicotinate | ≥95% |
| α-tocotrienyl nicotinyl succinate | ≥95% |
| α-tocotrienyl glycolyl nicotinate | ≥95% |
| α-tocotrienyl ferulyl nicotinate | 0% |

The term "comprising" whenever used in this document is intended to indicate the presence of stated features, integers, steps, components, but not to preclude the presence or addition of one or more other features, integers, steps, components or groups thereof.

Where singular forms of elements or features are used in the specification of the claims, the plural form is also included, and vice versa, if not specifically excluded. For example, the term "a compound" or "the compound" also includes the plural forms "compounds" or "the compounds," and vice versa. In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure also includes embodiments in which more than one, or all of the group members are present in, employed in, or otherwise relevant to a given product or process.

Furthermore, it is to be understood that the disclosure encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim.

Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

The disclosure should not be seen in any way restricted to the embodiments described and a person with ordinary skill in the art will foresee many possibilities to modifications thereof.

The embodiments described above are combinable.

REFERENCES

1. Muller, L., K. Theile, and V. Bohm, In vitro antioxidant activity of tocopherols and tocotrienols and comparison of vitamin E concentration and lipophilic antioxidant capacity in human plasma. Mol Nutr Food Res, 2010. 54(5): p. 731-42.

2. Yoshida, Y., E. Niki, and N. Noguchi, Comparative study on the action of tocopherols and tocotrienols as antioxidant: chemical and physical effects. Chem Phys Lipids, 2003. 123(1): p. 63-75.
3. Guo, M., et al., Inhibitory effects of Schisandra chinensis extract on acne-related inflammation and UVB-induced photoageing. Pharm Biol, 2016. 54(12): p. 2987-94.
4. Shibata, A., et al., Suppression of gamma-tocotrienol on UVB induced inflammation in HaCaT keratinocytes and HR-1 hairless mice via inflammatory mediators multiple signaling. J Agric Food Chem, 2010. 58(11): p. 7013-20.
5. Colombo, M. L., An update on vitamin E, tocopherol and tocotrienol-perspectives. Molecules, 2010. 15(4): p. 2103-13.
6. Manor, D., Morley, S., The α-Tocopherol Transfer Protein. In Vitamins & Hormones, Academic Press: 2007; Vol. 76, p. 45-65.
7. Gee, P. T., Unleashing the untold and misunderstood observations on vitamin E. Genes Nutr, 2011. 6(1): p. 5-16.
8. Parkhurst, R. M. and W. A. Skinner, Chromanols and Tocopherols, in Chemistry of Heterocyclic Compounds (eds G. P. Ellis and I. M. Lockhart). 2008. p. 59-137.
9. Heymann, E., et al., Organophosphate sensitive and insensitive carboxylesterases in human skin. Chem Biol Interact, 1993. 87(1-3): p. 217-26.
10. Montagna, W., Histology and cytochemistry of human skin. IX. The distribution of non-specific esterases. J Biophys Biochem Cytol, 1955. 1(1): p. 13-6.
11. Khodaeiani, E., et al., Topical 4% nicotinamide vs. 1% clindamycin in moderate inflammatory acne vulgaris. Int J Dermatol, 2013. 52(8): p. 999-1004.
12. Walocko, F. M., et al., The role of nicotinamide in acne treatment. Dermatol Ther, 2017; 30: e12481.
13. Rolfe, H. M., A review of nicotinamide: treatment of skin diseases and potential side effects. J Cosmet Dermatol, 2014. 13(4): p. 324-8.

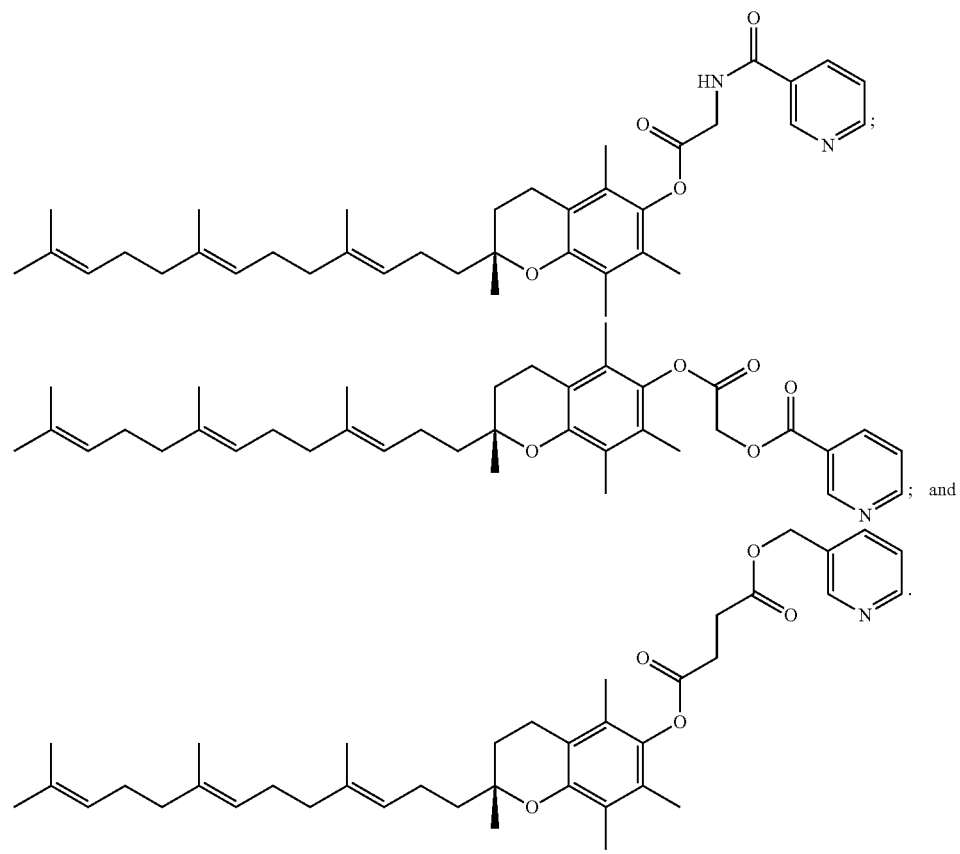

What is claimed is:

1. A compound of the following general formula (I)

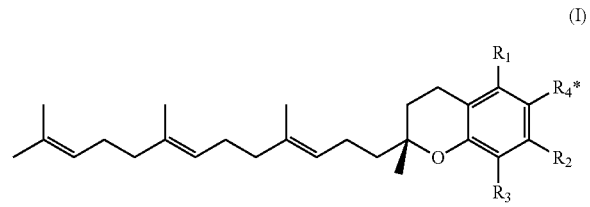

wherein $R_1$, $R_2$, $R_3$ and $R_4$ are independently selected from each other;

$R_1$ is H or $CH_3$;

$R_2$ is H or $CH_3$;

$R_3$ is H or $CH_3$;

$R_4$ is selected from

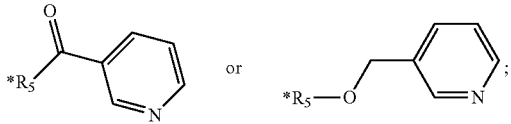

and

R5 is a glycolic diester residue, succinic diester residue, or a glycine amide ester residue.

2. A method of treatment in medicine or veterinary medicine comprising a step of administering the compound according to claim 1 to a human or animal subject wherein the administering step is for treatment of skin inflammation diseases, skin diseases, or skin disorders.

3. The method of treatment in medicine or veterinary medicine according claim 2 wherein the skin disorder is one or more of the following: acne, rosacea, or seborrheic dermatitis.

4. A pharmaceutical or cosmetic composition comprising at least one compound described in claim 1 in combination with at least one pharmaceutically or cosmetically acceptable excipient.

5. The pharmaceutical or cosmetic composition according to claim 4 wherein said composition comprises up to 20% by mass of the at least one compound compared to the total mass of the composition.

6. The pharmaceutical or cosmetic composition according to claim 4 wherein said composition comprises 0.01% to 10% by mass of the at least one compound compared to the total mass of the composition.

7. The pharmaceutical or cosmetic composition according to claim 4 wherein said composition comprises 0.1% to 5% by mass of the at least one compound compared to the total mass of the composition.

8. The pharmaceutical or cosmetic composition according to claim 4 wherein said composition comprises 0.1% to 2% by mass of the at least one compound compared to the total mass of the composition.

9. The pharmaceutical or cosmetic composition according to claim 4 wherein the composition is a topical composition.

10. The pharmaceutical or cosmetic composition according to claim 9 wherein the topical composition is a gel, a cream, a lotion, an ointment, a serum, a paste, or a foam.

11. A patch comprising the compound of claim 1, or a composition comprising the compound.

12. A method of non-therapeutic cosmetic enhancement comprising a step of applying the compound according to claim 1 to a human body.

13. The method according to claim 12 wherein the compound is applied as an anti-aging agent.

14. The compound according to claim 1, wherein the compound is selected from the following list: